US010368747B2

United States Patent
Grubis

(10) Patent No.: US 10,368,747 B2
(45) Date of Patent: Aug. 6, 2019

(54) SYSTEM AND METHOD OF WORKFLOW MANAGEMENT

(71) Applicant: General Electric Company, Schenectady, NY (US)

(72) Inventor: Matthew George Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/871,530

(22) Filed: Jan. 15, 2018

(65) Prior Publication Data

US 2018/0132719 A1    May 17, 2018

Related U.S. Application Data

(63) Continuation of application No. 14/945,558, filed on Nov. 19, 2015, now Pat. No. 9,901,251, which is a
(Continued)

(51) Int. Cl.
*A61B 5/00*       (2006.01)
*A61M 5/172*   (2006.01)
(Continued)

(52) U.S. Cl.
CPC .......... *A61B 5/0015* (2013.01); *A61B 5/0002* (2013.01); *A61B 5/0024* (2013.01); *A61B 5/01* (2013.01); *A61B 5/021* (2013.01); *A61B 5/024* (2013.01); *A61B 5/0205* (2013.01); *A61B 5/0402* (2013.01); *A61B 5/0476* (2013.01); *A61B 5/0488* (2013.01); *A61B 5/08* (2013.01);
(Continued)

(58) Field of Classification Search
CPC ....... A61B 5/02; A61B 5/0002; A61B 5/0024; A61B 5/7221; G06F 19/3418; G06F 19/34; A61M 5/1723
See application file for complete search history.

(56) References Cited

U.S. PATENT DOCUMENTS 6,525,656 B1   2/2003  Hahn
8,430,817 B1   4/2013  Al-Ali et al.
(Continued)

FOREIGN PATENT DOCUMENTS

| | | |
|---|---|---|
| CN | 101489316 A | 7/2009 |
| GB | 2489662 A | 10/2012 |
| WO | 2013036379 A1 | 3/2013 |

OTHER PUBLICATIONS

International Search Report and Written Opinion from corresponding PCT Application No. PCT/US2014/051198 dated Nov. 17, 2014.
(Continued)

*Primary Examiner* — Hongmin Fan
(74) *Attorney, Agent, or Firm* — Andrus Intellectual Property Law, LLP

(57) ABSTRACT

Wireless systems and methods include a plurality of peripheral electronic devices each having a wireless communication system. A processor is configured to establish an association confidence level indicative of a likelihood that a peripheral electronic device is associated to a monitored subject for each peripheral electronic device based on association criteria. Indicators are configured to communicate the association the association confidence level.

20 Claims, 5 Drawing Sheets

Related U.S. Application Data continuation of application No. 14/066,011, filed on Oct. 29, 2013, now Pat. No. 9,220,463.

(51) Int. Cl.

| | |
|---|---|
| A61N 1/39 | (2006.01) |
| A61B 5/0402 | (2006.01) |
| A61B 5/0476 | (2006.01) |
| A61B 5/11 | (2006.01) |
| A61M 16/00 | (2006.01) |
| A61B 5/021 | (2006.01) |
| A61B 5/024 | (2006.01) |
| G06F 19/00 | (2018.01) |
| A61B 5/0205 | (2006.01) |
| A61B 5/01 | (2006.01) |
| A61B 5/0488 | (2006.01) |
| A61B 5/08 | (2006.01) |
| A61B 5/145 | (2006.01) |
| G16H 40/63 | (2018.01) |
| H04W 4/38 | (2018.01) |
| H04W 4/80 | (2018.01) |
| G16H 50/20 | (2018.01) |
| G16H 50/30 | (2018.01) |
| H04W 4/02 | (2018.01) |

(52) U.S. Cl.
CPC ............ *A61B 5/11* (2013.01); *A61B 5/14542* (2013.01); *A61B 5/7221* (2013.01); *A61B 5/74* (2013.01); *A61M 5/1723* (2013.01); *A61M 16/0003* (2014.02); *A61M 16/0057* (2013.01); *A61N 1/3987* (2013.01); *G06F 19/34* (2013.01); *G16H 40/63* (2018.01); *G16H 50/20* (2018.01); *G16H 50/30* (2018.01); *H04W 4/027* (2013.01); *H04W 4/38* (2018.02); *H04W 4/80* (2018.02); *A61B 5/02055* (2013.01); *A61B 5/0816* (2013.01); *A61B 5/742* (2013.01); *A61B 5/746* (2013.01); *A61M 2205/18* (2013.01); *A61M 2205/3327* (2013.01); *A61M 2230/005* (2013.01)

(56) References Cited

U.S. PATENT DOCUMENTS

| | | | |
|---|---|---|---|
| 2007/0156626 A1* | 7/2007 | Roehm | A61B 5/0002 600/300 |
| 2008/0214944 A1* | 9/2008 | Morris | G06F 19/00 600/509 |
| 2009/0058635 A1 | 3/2009 | Lalonde et al. | |
| 2011/0137175 A1 | 6/2011 | Hossack et al. | |
| 2011/0305376 A1* | 12/2011 | Neff | G16H 40/20 382/128 |
| 2012/0203087 A1 | 8/2012 | McKenna et al. | |
| 2014/0089007 A1* | 3/2014 | Sim | G06F 19/3418 705/3 |

OTHER PUBLICATIONS

Machine Translation and First Office Action and Search issued in connection with corresponding CN Application No. 201480060112.4 dated Nov. 1, 2018, 27 pages.

\* cited by examiner

SYSTEM AND METHOD OF WORKFLOW MANAGEMENT

CROSS REFERENCE TO RELATED APPLICATION

This application is a continuation of U.S. application Ser. No. 14/945,558, filed Nov. 19, 2015, which application was published on May 5, 2016, as U.S. Publication No. 20160120406, which application is a continuation of U.S. application Ser. No. 14/066,011, filed Oct. 29, 2013, which application was published on Apr. 30, 2015, as U.S. Publication No. U.S. 20150119651, and granted on Dec. 29, 2015 as U.S. Pat. No. 9,220,463, which applications are incorporated herein by reference in their entireties.

BACKGROUND

The present disclosure is related to the field of workflow management. More specifically, the present disclosure is related to systems and method of managing workflow based upon an association between at least one wireless sensor and a monitored patient.

Monitoring vital signs is an important part of patient care as the general or particular health of the patient is determined, in part, through measurement and interpretation of key physiological indicators. Well-known parameters of patient health include blood pressure, hemoglobin saturation ($SPO_2$), and features of the electrocardiogram (ECG). However, the utilization of physiological instrumentation to obtain these measurements at the bed side of a patient also possess well-known burdens to the clinical environment. The presence of cables, catheters, and tubing connecting the patient and sensors to the instrumentation configured to provide all monitoring or therapeutic care can diminish productivity and the quality of patient care. For example, rotating a patient to alleviate bed sores or patient ambulation about the room can be problematic if the patient is saddled with tethered devices. Procedural delays stemming from cable management also contribute to a great percentage of time dedicated to routine, mundane tasks not directly related to treatment of the patient's illness.

Wireless communication technology leveraged to patient monitoring and therapy may at least mitigate some of the problems associated with cable clutter and device management. With instrumentation becoming wireless, the management of such devices is eased. In addition, wireless instrumentation/devices greatly reduce the burden associated with cable management.

Wireless patient monitoring networks, however, bring new problems that need to be addressed for proper implementation of a monitoring regime. In many instances, whether using a wireless monitoring system or a wired system, elements of the system communicate with at least one central management device. In the hospital environment, this management device is often used to relay monitored information to an infrastructure that allows health care professionals to analyze the monitored information from an outside location (e.g. a nurse station). In other wireless systems, the management device may be integrated with a central processing unit that analyzes the incoming device information. When cables are removed from these devices, a user of the system can no longer safe guard that the devices are properly connected to the patient to be monitored by the management device by simply ensuring that the cables extend from the management device to the correct patient. That is, without cables, a health care provider or other operator lacks the visual cues associated with cables to assure that the sensing devices are properly connected to the proper patient to be monitored by the management device. Alternatively, as wireless sensing systems proliferate in a care setting, wireless sensing devices may inadvertently become communicatively connected with a management device associated with another patient. Again, without the visual cues of the cable, a healthcare provider or other operator lacks a tool for fast and accurate confirmation that the management device is receiving physiological data from a specified patient and that patient only.

BRIEF DISCLOSURE

An exemplary embodiment of a wireless system includes a plurality of peripheral electronic devices each having a wireless communication system. A hub includes a wireless communication system. The hub is in wireless communication with the peripheral electronic devices. A processor is configured to establish an association confidence level for each peripheral electronic device based on a plurality of association criteria. The association confidence level for each peripheral electronic device is reflective of the likelihood that a peripheral electronic device is associated to a monitored subject. Each of a plurality of indicators are configured to communicate the association confidence level for a peripheral electronic device.

In an exemplary embodiment of a wireless patient monitoring system, a plurality of peripheral electronic devices each have a wireless communication system and a sensor. Each of the plurality of peripheral electronic devices is configured to be secured to a monitored patient and configured to acquire physiological data from the monitored patient. A hub includes a wireless communication system. The hub is in wireless communication with the peripheral electronic devices to receive the physiological data acquired by the peripheral electronic devices. A processor is configured to register each of the plurality of peripheral electronic devices to the monitored patient. The processor is configured to receive the physiological data from the hub. The processor is configured to establish an association confidence level for each peripheral electronic device. The association confidence level is indicative of a likelihood that the physiological data acquired by the peripheral electronic device is from the monitored patient. Each of a plurality of indicators is configured to communicate the association confidence level for a peripheral electronic device of the plurality of peripheral electronic devices.

An exemplary embodiment of a method of workflow management in a wireless patient monitoring system includes providing a plurality of peripheral electronic devices. Each of the plurality of peripheral electronic devices includes a sensor configured to acquire physiological data from a patient and a communication system. A processor registers each of the plurality of peripheral electronic devices to a monitored patient. Physiological data acquired by each of the peripheral electronic devices is received at the processor. An association confidence level is determined for each of the peripheral electronic devices based at least in part upon the received physiological data. A perceptible indication of the determined association confidence levels is produced.

DETAILED DISCLOSURE

Figure 1:
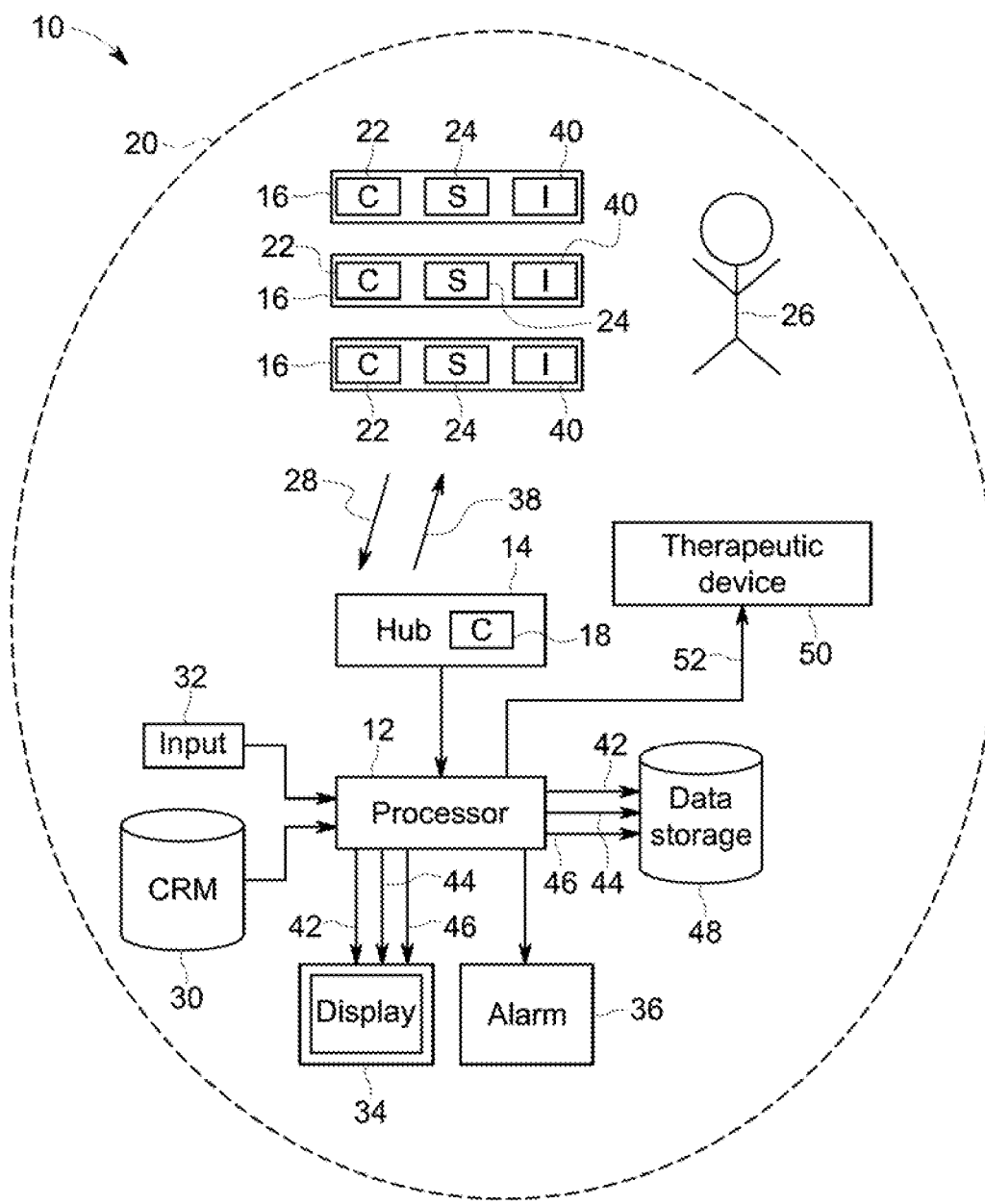
FIG. 1 is a schematic diagram of an exemplary embodiment of a wireless system.

FIG. 1 is a schematic diagram of a wireless system 10. The wireless system 10 includes a processor 12 that is configured in the manner as disclosed herein to receive a plurality signals acquired by the wireless system 10, evaluate the signals, and initiate a response. The wireless system 10 further includes a hub 14 that is configured to communicate both with the processor 12 and with a plurality of peripheral electronic devices 16. It will be understood that in embodiments, the hub 14 may be an independent device that is communicatively connected to the processor 12, while in other embodiments the hub 14 may be integrated into a single device with the processor 12.

The hub 14 includes a wireless communication system 18 that exemplarily creates a communication area or range 20 within which the hub 14 may be communicatively connected with one or more of the peripheral electronic devices 16 which similarly may comprise a wireless communication system 22. It will be understood that the wireless communication systems 18, 22 respectively of the hub 14 and the peripheral electronic devices 16 will be communicatively compatible and in an embodiment are radio frequency (RF) wireless communication devices. However, it will be understood that in alternative embodiments, the wireless communication systems 18, 22 may include optical, magnetic, ultrasound, visible light, infrared, or other forms of wireless communication systems.

While embodiments of the peripheral electronic devices 16 may include other components as described in further detail herein, each of the peripheral electronic devices 16 include at least one sensor 24 that is operable to acquire or measure at least one parameter or signal. In the present disclosure, the exemplary embodiment and application of a health care setting is used for descriptive purposes, although, it will be recognized that alternative embodiments of the systems and methods as disclosed herein may be used in conjunction with other applications in which a plurality of wireless peripheral electronic devices must be managed. Thus, in the exemplary embodiment given herein, the sensors 24 may be physiological sensors that are configured to acquire physiological data from a patient to be monitored 26. In non-limiting embodiments, the sensors 24 may include heart rate, pulse rate, temperature, electrocardiogram (ECG), blood pressure (e.g. NIBP), respiration, physical movement, electroencephalogram (EEG) and others as may be recognized by a person of ordinary skill in the art.

In embodiments, the sensors of the peripheral electronic devices measure or otherwise acquire at least one physiological parameter from the patient 26. The wireless communication system 22 of the peripheral electronic devices works with the wireless communication system 18 of the hub 14 to wirelessly transmit the acquired physiological data 28 from each of the peripheral electronic devices 16 through the hub 14 to the processor 12.

The processor 12 is connected to at least one computer readable medium 30. In embodiments, the processor executes computer readable code stored on the computer readable medium 30 as software or firmware. The execution of the computer readable code causes the processor 12 to operate in a manner such as to carry out the operations and functions as described herein. In an exemplary embodiment, the computer readable medium is an integral part of the processor 12.

In still further embodiments, the processor is communicatively connected to the at least one computer readable medium 30. Data is stored on the computer readable medium 30 such data may include information regarding system data, association criteria as described in further detail herein. In embodiments disclosed herein particular combinations of association criteria as may be used depending upon the patient, the peripheral electronic devices used, or the patient diagnosis, etc., and/or a weight or priority assigned to one or more of the association criteria.

An input device 32 is further connected to the processor 12 wherein by a clinician or technician can enter information including information regarding the patient to be monitored, the peripheral electronic devices used, the physiological condition of the patient, the association criteria to be used in evaluation of the association between the peripheral electronic devices, or a weighting to be used in evaluating such association criteria. In some embodiments as disclosed herein, the input device 32 may be used by the clinician or technician to initially register each of the peripheral electronic devices 16 to the patient to be monitored 26. This initial registration may include the use of a bar code scanner or entering some other type of identifying information from the peripheral electronic device or the execution of a registration process carried out by the wireless communication system 18, 22 of the peripheral electronic devices 16 and the hub 14, respectively.

The processor 12 further operates a graphical display 34 that visually presents an indication of the confidence level indicative of the association between each of the peripheral electronic devices and the monitored patient determined in a manner as described in greater detail herein. The graphical display 34 operates to present such information in a graphical user interface (GUI) which may be configured in a variety of manners to visually convey this information. In embodiments, the graphical display 34 may be a flat panel display or may be a display associated with a laptop or tablet computer, or a display of a mobile device. In still further embodiments, the display 34 may have touch sensitive capabilities and as such operate as both the display 34 as well as the input device 32. In still further embodiments, the display 34 may further be operated by the processor 12 to present some or all of the physiological data acquired from the monitored patient by the plurality of peripheral electronic devices 16.

The processor 12 is further connected to an alarm 36. The alarm 36 may be an audible or visual alarm that produces an alert indicative of the confidence level in the association between each of the peripheral electronic devices and the monitored patient. In an embodiment, the alarm 36 may only provide an indication when the confidence level in the association between a peripheral electronic device and the monitored patient falls below a predetermined threshold as determined by the processor 12. The alarm 36 may include a light indicator such as an LED; however, in alternative embodiments, the alarm 36 may be generated sound or a textual message sent to one or more care providers through text messaging, e-mail or other known communication platforms.

In an alternative embodiment, the processor 12 further transmits a signal 38 indicative of the confidence level to each of the respective peripheral electronic devices 16 through the communication system 18 of the hub 14 and the respective communication system 22 of the peripheral electronic device 16. Each of the peripheral electronic devices 16 include an indicator 40 that operates to present the association confidence level received from the processor 12. In an embodiment, the indicator 40 may be a noise making device, a light emitting diode (LED) or other visual device, or a tactile device such as a vibration unit that operates in a manner such as to notify a clinician or technician of the association confidence level in the association between the peripheral electronic device and the monitored patient. In one non-limiting embodiment, the indicator 40 is a light source that is configured to emit light at an intensity level that is proportional to the received association confidence level. In another embodiment, the indicator 40 is a light source, that is configured to emit light within a first color spectrum, exemplarily green if the confidence level is above a first threshold, the light source emits light within a second color spectrum, exemplarily yellow, if the confidence level is at or below the first threshold and above a second threshold, and emits light within a third color spectrum, exemplarily red, if the confidence level is at or below the second threshold. In such exemplary embodiments, the light source may be one or more LEDs configured to emit light in the required colored spectrum.

In a still further embodiment, the indicator 40 is an audible alarm that is configured to emit an audible signal when the confidence level is below a predetermined threshold.

As will be described in further detail herein, in embodiments, the processor 12 may operate to provide an automated diagnosis or other types of automated medical guidance based upon the received physiological data and other sources of information regarding the patient, including, but not limited to the medical information found in the patient's electronic medical record (EMR). Non-limiting examples of such automated diagnosis or other automated medical guidance may include automated indications of the patient's condition based upon the acquired physiological data, suggested treatments, therapy, or recommendations to the patient based upon the received physiological data. In one such embodiment, the processor 12 provides the physiological data 42 acquired by the peripheral electronic devices 16, the determined association confidence level 44 in the association between each of the peripheral electronic devices 16 and the monitored patient 26, and the automated guidance 46 as described above to the graphical display 34 for presentation to the clinician. As will be described further therein, the presentation of at least a portion of the physiological data and the association confidence levels in the acquisition of that physiological data can help to facilitate a clinician's evaluations of any automatedly generated guidance based wholly or in part upon the received physiological data. In alternative embodiments as described in further detail herein, the automated guidance 46 may only be presented at the graphical display 34 if the underlying physiological data is acquired at an association confidence level above a predetermined threshold that the physiological data is associated with the monitored patient 26.

The processor 12 is further connected to data storage 48 wherein the data storage 48 may be located on a computer readable medium that is either local or remote from the processor 12. Thus, the data storage 48 may be communicatively connected to the processor 12 through a local hospital intranet or a wide area network exemplarily over the Internet. In one embodiment, the data storage 48 is exemplarily an electronic medical record (EMR) of the monitored patient and the processor 12 and receives and stores the acquired physiological data 42 received from the plurality of peripheral electronic devices, the association confidence levels 44 and any automated guidance 46 determined by the processor 12.

In an alternative embodiment as will be described in greater detail herein, the acquired physiological data 42 may be appended with the determined association confidence level 44 and the appended values stored together in the EMR.

In still further embodiments, the patient 26 is connected to at least one therapeutic device 50 that provides therapy or treatment to the patient. In embodiments, the therapeutic device 50 receives a control signal 52 from the processor 12. In response to the control signal 52, the therapeutic device 50 may take one or more automated therapeutic actions. The processor 12 generates the control signal 52 in part based upon at least some of the received physiological data. In non-limiting embodiments, the therapeutic device 50 may be a defibrillator, a drug pump, an intravenous (IV) solution pump, or a ventilator which may operate to provide an automated therapy to the patient in accordance with the received control signal 52. In an exemplary embodiment, the defibrillator may perform an automated action upon detection of an arrhythmic pattern in the ECG waveform of the patient. In a further embodiment, a drug pump or IV solution pump may be delivered to increase or decrease a rate of delivery of a medication or fluid in response to a detected change in physiological condition. In embodiments as will be described in further detail herein, the processor may operate in conjunction with the determined association confidence levels for each of the peripheral electronic devices that acquire the physiological data and only produces a control signal 52 in order to initiate the delivery of the automated therapy if the association confidence levels for the peripheral electronic devices that acquired the physiological data that resulted in initiation of the automated therapy indicate a high confidence level in being associated with the monitored patient who will receive the automated therapy. In such embodiment, this safety feature helps to ensure that if a peripheral electronic device becomes connected to an alternative patient then the monitored patient, that alternative patient's physiological parameters do not result in the delivery of an automated therapeutic response to the wrong patient.

Figure 2:
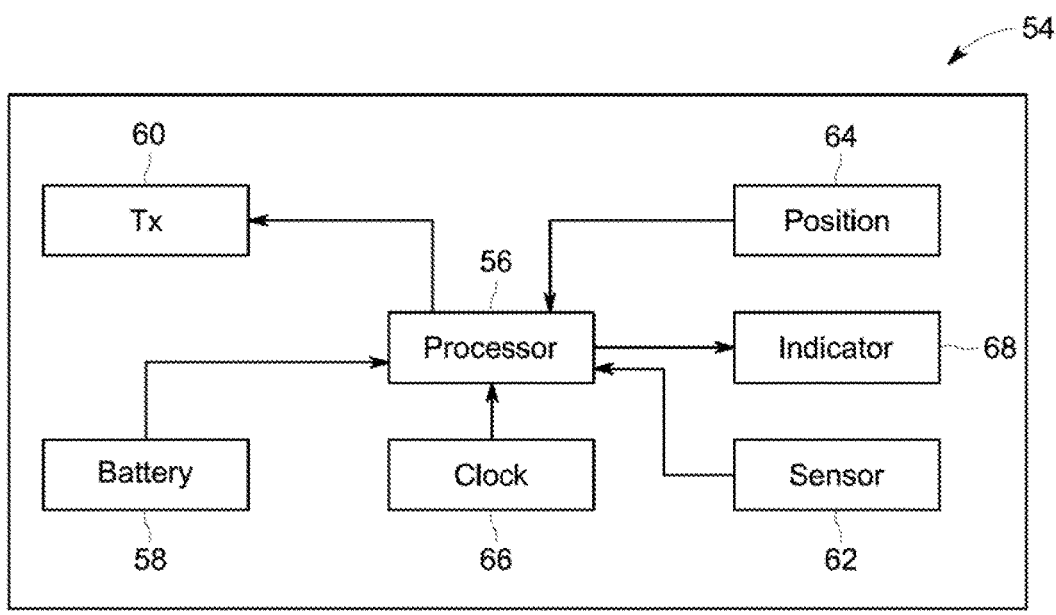
FIG. 2 is a schematic diagram of an exemplary embodiment of a peripheral electronic device.

FIG. 2 depicts a more detailed exemplary embodiment of a peripheral electronic device 54 such as may be used in conjunction with the wireless system 10 depicted in FIG. 1. The peripheral electronic device 54 includes a processor 56 that executes software or firmware stored at the processor 56 in order to carry out the functions as described in further detail herein. The peripheral electronic device 54 further includes a battery 58 that provides power to the processor 56 and other components of the peripheral electronic device requiring energization, either directly or indirectly from the battery 58. In an embodiment, the peripheral electronic device 38 may be constructed such that the battery 58 is replaceable or rechargeable. In such embodiments, the peripheral electronic device 54 may be configured to be reused and the battery replaced or recharged in order to extend the life of the peripheral electronic device 54. In other embodiments, the peripheral electronic device 54 may be disposable after the power is drained from the battery 58. Depending upon such embodiments, the processor 56 may monitor either the remaining battery life, elapsed time or elapsed usage since battery replacement or recharge, battery output voltage, or other such measurement of remaining battery life.

As described above, the peripheral electronic device 54 is configured to be secured to the patient to be monitored and to wirelessly transmit physiological data 38 through an interaction between a wireless communication system 18 of a hub 14, with a wireless communication system 22 of the peripheral electronic device 16 (FIG. 1). In the exemplary embodiment of FIG. 2 the peripheral electronic device 54 includes a transmitter 60 in order to broadcast or otherwise transmit information from the peripheral electronic device as described above, the transmitter 60 may include any of a variety of known communication transmitters, including, but not limited to radio frequency, infrared, visible light, or ultrasonic, or other known transmission implementations.

The peripheral electronic device 54 is configured with a sensor 62. The sensor 62 is configured to acquire or otherwise measure a physiological parameter from the patient. Non-limiting examples of physiological parameters that may be measured or acquired, include biopotentials such as electrocardiogram (ECG), electromyogram (EMG), and electroencephalogram (EEG). The sensor 62 may also be configured to acquire other physiological parameters such a heart rate, oxygen saturation ($SPO_2$), blood pressure, such as acquired by noninvasive blood pressure (NIBP) monitoring, respiration rate, motion detection, or temperature. However, these are merely exemplary of the types of sensors that may be incorporated into the peripheral electronic device 54 and are not intended to be limiting.

Embodiments of the peripheral electronic device 54 may further include a position detector 64. In an exemplary embodiment, the position detector 64 may be a global positioning system (GPS) detector. The position detector 64 further provides the location of the peripheral electronic device 54 and can be transmitted by the transmitter 62 along with the physiological data collected by the sensor 64.

The peripheral electronic device 54 may further include a clock 66 where the clock 66 may be a separate component found in the peripheral electronic device 54, or may be an integral component associated with the processor 56. In embodiments, the clock 66 can operate such as to measure an elapsed time since initial registration of the peripheral electronic device 16 with the processor 12 FIG. 1 to the monitored patient as described above. In an alternative embodiment, the clock 66 may be used to measure the operational time since the last battery replacement or recharge as also discussed above.

The peripheral electronic device 54 further may include an indicator 68 connected to the processor 40. In embodiments, for notification purposes, the indicator 52 may be a noise making device, an LED or other visual devices or a tactile device such as a vibration unit for notifying a clinician or technician of the association status of the peripheral electronic device 54 with the monitored patient through sound, light, or tactile methods.

Figure 3:
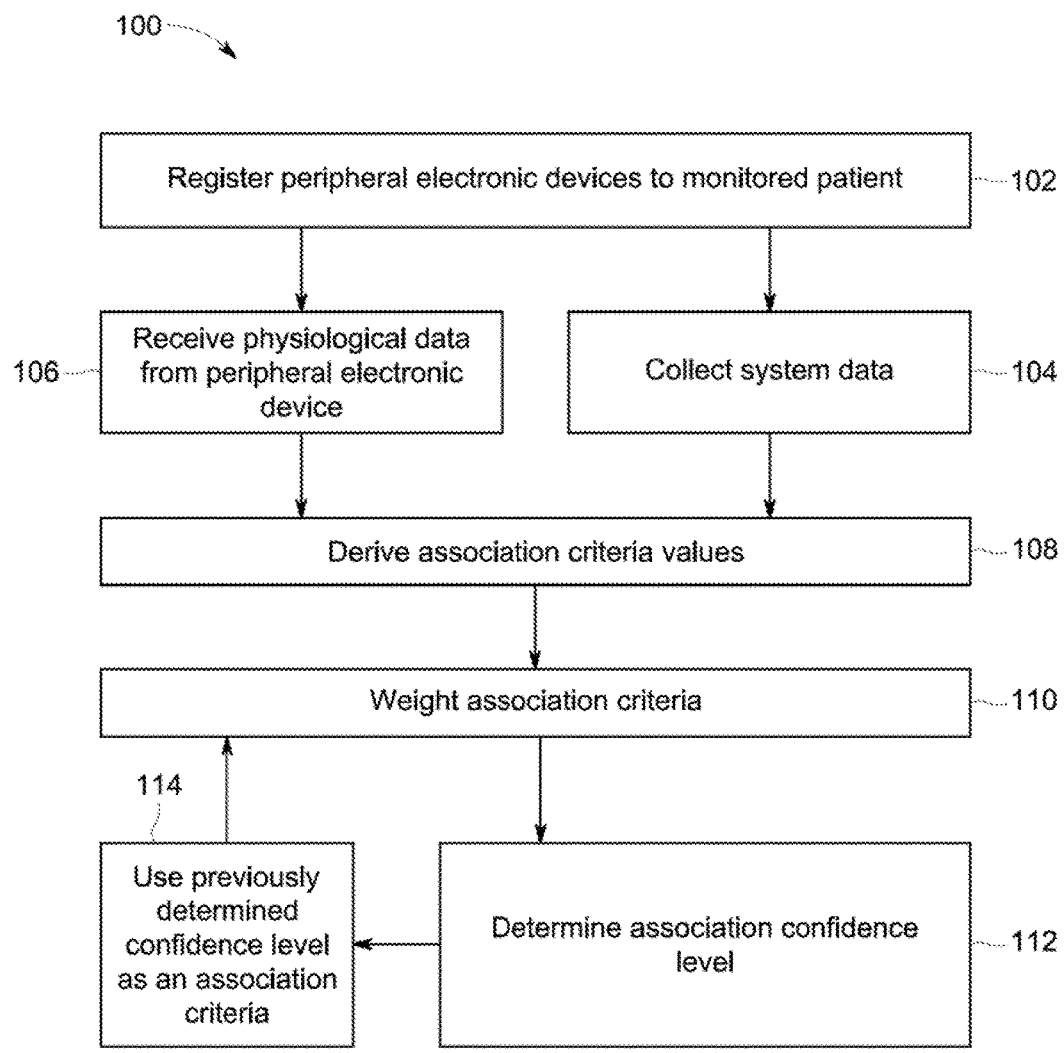
FIG. 3 is a flow chart that depicts an exemplary embodiment of a method of evaluating an association confidence level between a peripheral electronic device and a monitored patient.

FIG. 3 is a flow chart that depicts an exemplary embodiment of a method 100 of evaluating an association between a peripheral electronic device and a monitored patient. The method 100 may be carried out by a wireless system, such as wireless system 10 described above with respect to FIG. 1; however, it will be understood that in alternative embodiments, an association confidence level can be determined in other ways. In an embodiment, association criteria of at least one system attribute and at least one sensor attribute are evaluated to determine an association confidence level between the peripheral electronic device and the monitored patient. Depending upon the sensor itself, the type of wireless communication system used by the sensor, and the components available in the peripheral electronic device (e.g. clock, position device, as described above), certain system and sensor attributes as described in further detail herein may be more relevant or applicable in calculating the confidence level. Alternatively, some association criteria may not be available due to the constraints of the peripheral electronic devices, sensors, or the wireless system. As such, for any given system or monitored patient, a subset of the overall set of possible association criteria will exist.

At 102, each peripheral electronic device of the plurality of peripheral electronic devices is registered to a monitored patient. It will be recognized that in the description herein, the peripheral electronic devices registered at 102, may include a sensor and be configured to be secured to a patient and to transmit physiological data acquired by the sensor to a processor in the wireless system. As described above, the peripheral electronic devices may be registered by one or more clinician or technician inputs into the wireless system in order to provide an initial association between each of the plurality of peripheral electronic devices and the patient to be monitored. Once the wireless sensors are registered and secured to the monitored patient, the processor may begin to receive physiological data as acquired by the sensors through the wireless system.

At 104 system data are collected from the system. The system data are values and/or conditions that are related to the association of the peripheral electronic device to the monitored patient, but are a part of the wireless system rather than physiological data acquired from the patient. Examples of association criteria that may be dependent upon system data collected at 104 can include length of time since registration of a peripheral electronic device to a patient, an RF signal strength, an elapsed time that peripheral electronic device is confirmed off of a patient, activity types, a number of communication errors, a battery state or condition, a known operation lifetime of the peripheral electronic device, a location, exemplarily a GPS location, a proximity beacon, elapsed time on the patient, identified instances of sensor disconnection from the patient, movement of the peripheral electronic device, or a location of an accessory or other device associated with the patient; however, these are merely exemplary of the types of association criteria that may be collected from the system.

At 106 physiological data acquired by the sensors of the peripheral electronic devices are received by the processor. The peripheral electronic devices transmit the physiological data to the processor as described above through the wireless system. As further described above, a variety of physiological data may be acquired by sensors in peripheral electronic devices associated to each patient. The received physiological data may include, but is not limited to ECG, EMG, EEG, temperature, respiration, $SPO_2$, blood pressure, movement, heart rate, pulse rate, or others. Depending upon the diagnosis and treatment being received by the patient, the patient may be monitored to acquire various physiological data. In embodiments, the acquired physiological data may be in the forms of waveforms, traces, or other signals that must be processed to obtain values meaningful to determining an association confidence level.

At 108 association criteria values are derived from the physiological data and the system data. The received physiological data is processed to derive association criteria values. The association criteria values derived from the physiological data may include such association criteria values that are representative of a confidence in the association status between an peripheral electronic device and the monitored patient by providing a measure of the coincidence or congruity between physiological data acquired between sensors of different peripheral electronic devices in the plurality of peripheral electronic devices.

In one example, a plurality of ECG leads may be acquired by separate peripheral electronic devices and an ECG signal, waveform characteristic, or heart rate as indicated by each of the ECG leads are compared to determine whether each ECG signal is consistent or inconsistent with that obtained from the other leads. If the ECG signal obtained from one of the peripheral electronic devices is inconsistent with the other ECG signals from the peripheral electronic devices associated with the monitored patient, then that peripheral electronic device will have a lower association criteria value to reflect the reduced confidence that that peripheral electronic device is associated with the monitored patient. Similar comparisons may be made across physiological parameters, exemplarily, heart rate as determined through ECG signals acquired by peripheral electronic devices, and $SPO_2$ peripheral electronic devices and an NIBP peripheral electronic device may all be compared to evaluate the consistency or inconsistency of the heart rates between each of these peripheral electronic devices to evaluate their association to the monitored patient.

In a still further embodiment, one physiological parameter measured by a sensor of one of the peripheral electronic devices may produce a known artifact in the signal acquired by a sensor of a peripheral electronic device configured to acquire another physiological parameter. Exemplarily, a known cardiac artifact may appear in any of a number of physiological parameter signals, including, but not limited to a respiration monitor, EEG waveform, or EMG waveform. Similarly, a respiration artifact may be known to be present in an acquired ECG signal. In an alternative embodiment, the monitored physiological data, e.g. heart rate, as acquired from an ECG signal is compared to the known cardiac artifact in the physiological data acquired by another peripheral electronic device and an association criteria value derived to reflect this consistency or inconsistency, of this comparison between the physiological data of the peripheral electronic devices.

In an embodiment, exemplary association criteria values derived from system data may include a numerical representation of RF signal strength or an association confidence based upon the length of time since the peripheral electronic device has been registered to the monitored patient. A further association criteria value may be a numerical representation of a confidence that the peripheral electronic device is associated with the patient to be monitored. For example, if the RF signal strength of one peripheral electronic device is noticeably weaker or stronger than those of other peripheral electronic devices registered to the same patient, this may indicate low confidence while congruency between all RF signals of the peripheral electronic devices registered to the same patient may be a sign of increased confidence. Similarly, as the length of time since the initial registration of the peripheral electronic device, or length of time since a clinician's physical verification of connection of the peripheral electronic device to the monitored patient gets longer, the confidence in the association decreases. Similarly, if a peripheral electronic device extends beyond an expected life, battery power, battery life, or recommended replacement time, these may all be indications of a lowered confidence in the association status. In other examples, if a sensor experiences a large number of communication errors or is in a location apart from other peripheral electronic devices registered to the monitored patient, these may be indicative of a reduced confidence in the association status of the peripheral electronic device.

At 110 the association criteria are weighted. A weighting criteria is determined based upon the overall strength of each of the association criteria as well as the total number of association criteria available in the subset of available association criteria. Weighting criteria may also be further determined based upon the derived values of the association criteria. As noted above, not all association attributes may be used or available in all instances. Specifically, based upon the types of sensors or types of peripheral electronic devices and the types and amount of physiological data collected, only a subset of the possible association criteria will be available. The relative strength of the association criteria in determining an association confidence level between a peripheral electronic device and a monitored patient may be considered in weighting the association criteria. For example, an association criteria such as elapsed time since initial registration may be heavily weighted if the elapsed time is short, but may receive a lesser weighting as the elapsed time lengthens. In an embodiment, the weighting may again increase, as an indicator of decreased confidence, if the elapsed time exceeds an expected procedure duration or peripheral electronic device expected usage. It is to be noted that in some embodiments only physiological data based association criteria may be used while in other embodiments a combination of association criteria based upon system data and physiological data may be used. It is possible that the number of association criteria changes and the weighting criteria changes during a single device-patient association session. As will be discussed in further detail herein, embodiments of the method 100 may be repeated periodically in order to produce an updated evaluation of the association between the peripheral electronic devices and the monitored patient and the weighting of the association criteria may change from cycle to cycle. These changes may be due to the addition or subtraction of peripheral electronic devices, length of time elapsing between evaluation cycles.

At 112 an association confidence level is determined for each peripheral electronic device based upon the weighted association criteria values. In an embodiment, the weighted association criteria values are summed on a sensor by sensor basis. This summation may produce a raw indication of the association between each of the individual peripheral electronic devices of the plurality and the patient to be monitored by those peripheral electronic devices. The association confidence level determined at 112 may exemplarily be a normalized value of all of the summed weighted association criteria values for that peripheral electronic device. In an alternative embodiment, the association confidence level may be normalized on an S curve. Alternatively, an association confidence level may be exemplarily determined into categories such as high, medium, and low association confidence level. This categorization may exemplarily be performed by comparing a raw association confidence level to a plurality of thresholds.

In embodiments, as mentioned above, the association confidence level for each peripheral electronic device may be periodically recalculated such as to update these determinations. In one embodiment, once an association confidence level has been calculated at 112 this previously calculated association confidence level may be used at 114 as another association criteria is weighted and incorporated back into the method 100.

Figure 4:
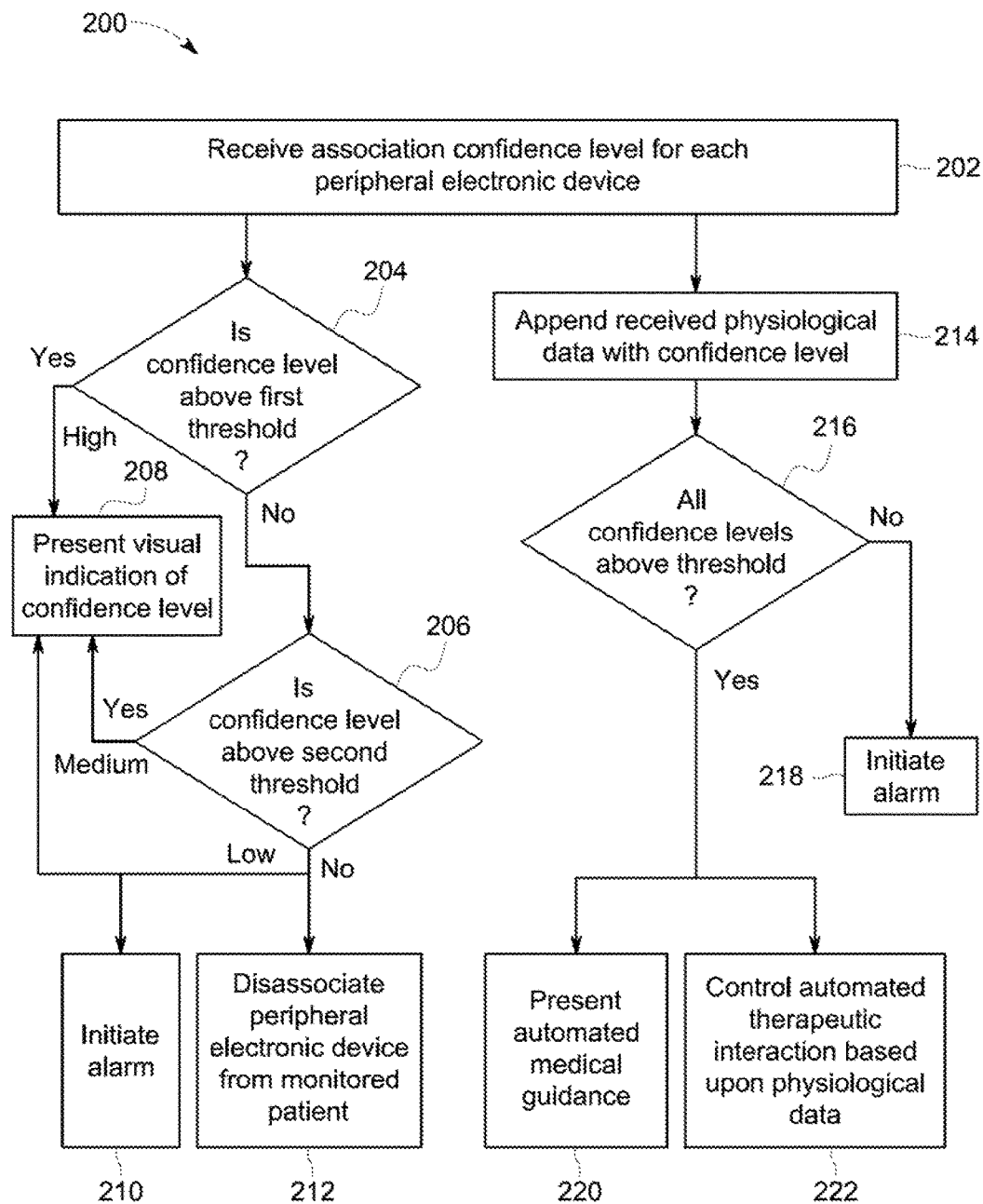
FIG. 4 is a flow chart that depicts an exemplary embodiment of a method of responses to an association confidence level.

FIG. 4 is a flow chart that depicts an exemplary embodiment of a method 200 of workflow management based upon an association confidence level representative of an association between each of a plurality of peripheral electronic devices and a monitored patient. As reflected in the method 200 a number of alternative responses or actions may be taken once an association confidence level has been determined. In embodiments, it will be recognized that one more of these responses may occur simultaneously or sequentially or that other types of responses are also contemplated herein.

The method 200 begins at 202 when an association confidence level for each peripheral electronic device is received. In an embodiment, the association confidence levels for each of the peripheral electronic devices may be determined in the manner as explained above with respect to FIG. 3, although, in other embodiments, the association confidence level may be determined in other ways and still be used in the methods as described herein.

In an embodiment, the association confidence levels for each peripheral electronic device are compared to a plurality of thresholds in order to categorize the association confidence levels and to direct workflow responses. Exemplarily, the association confidence levels are compared to a first threshold at 204 and a second threshold at 206.

At 204 the association confidence level is compared to a first threshold. This first threshold may exemplarily be representative of a high confidence in the association between that peripheral electronic device and the monitored patient. In a merely exemplary embodiment, the association confidence level is normalized on a scale of 0 to 100, the first threshold may exemplarily be a normalized score of 90 although the first threshold may be any value as deemed medically or institutionally relevant.

Figure 5:
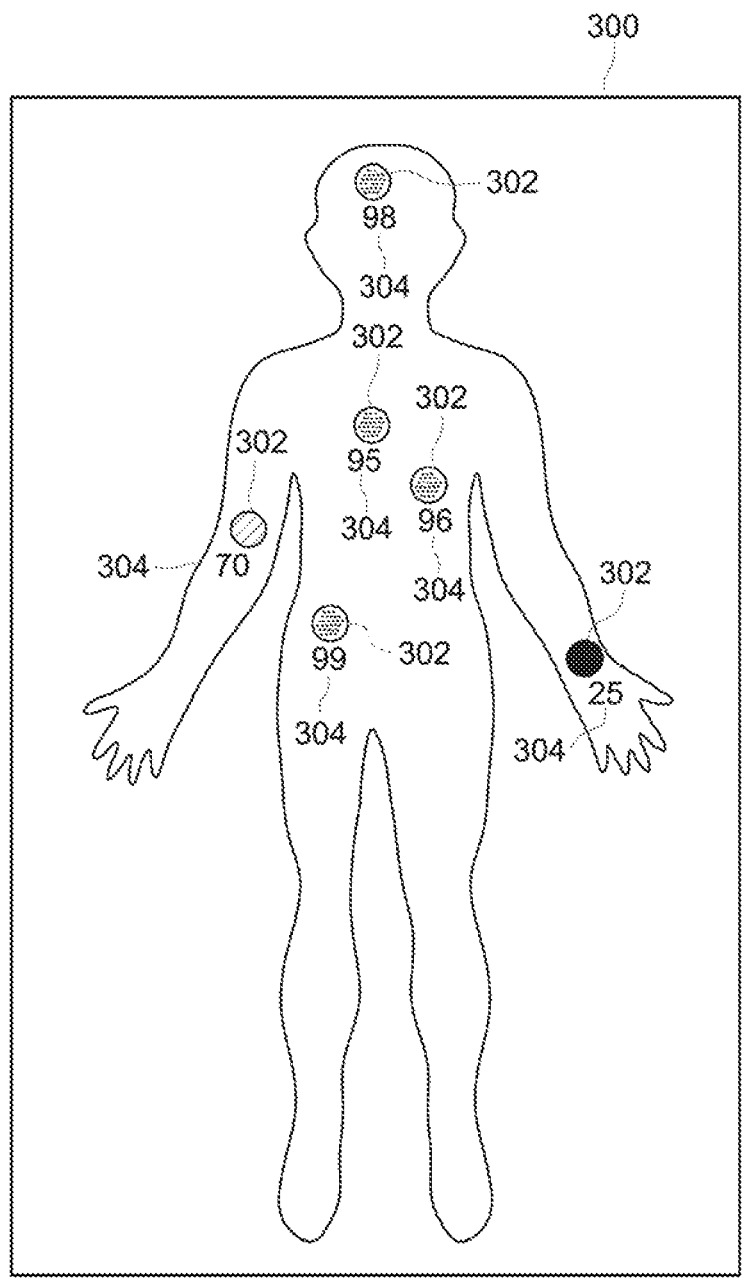
FIG. 5 depicts an exemplary embodiment of a graphical user interface in accordance with an exemplary embodiment.

At 208 a visual indication of the confidence level may be presented, exemplarily as in any of the manners as disclosed above. As specific non-limiting examples, the confidence level may be presented in a graphical user interface presented on a graphical display and such presentation may include both a presentation of the numerical association confidence level value and/or a categorization of such association confidence level. FIG. 5 depicts a non-limiting example of such a graphical user interface display 300. In still further embodiments, the association confidence level may be transmitted back to peripheral electronic device and a visual indicator, exemplarily one or more light emitting diodes (LEDs) may be illuminated at a color or intensity representative of the association confidence level.

At 206 if the association confidence level is below the first threshold at 204 then the association confidence level is compared to a second threshold. If the association confidence level is above this second threshold, the association confidence level may be exemplary denoted as a medium confidence and presented as described above with respect to 208. In a non-limiting embodiment, the second threshold may be 70 on a normalized scale of 0-100, while in an alternative embodiment the second threshold may be 50 on a normalized scale of 0-100. If the association confidence level is not above the second threshold, then the association confidence level may be categorized as a low confidence in the association between that peripheral electronic device and the monitored patient, and such visual indication of the confidence level presented at 208 as described above.

Additionally, if the association confidence level is below the second threshold, further actions may be undertaken in response to the low confidence in the association between the peripheral electronic device and the monitored patient. Exemplarily, an alarm may be indicated at 210. The alarm may exemplarily be a visual, audio, or tactile alarm that initiated to alert a clinician or a technician of the reduced confidence in the association between the peripheral electronic device and the monitored patient. Such alarms may exemplarily be presented at a graphical user interface, at the peripheral electronic device, or may take the form of a textual or other communication to a clinician or technician notifying them of the determined low confidence.

In an embodiment the alarm initiated at 210 is exemplarily directed or configured to prompt a response by a clinician or technician. In one exemplary embodiment, the clinician or technician is prompted to locate and verify the physical placement and attachment of the low confidence peripheral electronic device to the monitored patient. Such prompt may include a prompt for the clinician or technician to reregister or otherwise verify that the peripheral electronic device is properly attached to the monitored patient. This reregister or verification may be used as or update a value of an association criteria, resulting in an improved association confidence level and removal of the alarm.

While the initiation of an alarm at 210 is depicted in FIG. 4 as being initiated only after the determination of a low confidence level, in an alternative embodiment, there may be a plurality of states or stages of confidence level and various set alarms or alarms responses may escalate with the escalation of the determined confident level.

A determination of a low confidence level may also result in the disassociation of a peripheral electronic device from a monitored patient at 212. If the association confidence level is determined to be a low confidence, exemplarily below the second threshold at 206, that peripheral electronic device may be disassociated from the monitored patient at 212. In such an embodiment, the physiological data obtained by the peripheral electronic device may still be temporarily stored, but may not be immediately entered into the patient's electronic medical record or presented on a graphical display with the other physiological data obtained from the monitored patient. This can be done as a precaution such that physiological data in which there is a low confidence to have emanated from the monitored patient is not immediately stored or presented in conjunction with the monitored patient. Since the confidence in this physiological data emanation from the monitored patient is low, in embodiments it may be preferable to take this precaution such that medical decisions, diagnosis, and other such determinations are not made based upon this physiological data. If, at a later time, the peripheral electronic device is verified to have been associated with the monitored patient at the time the data was acquired, the physiological data may be restored to the patient's electronic medical record. In an alternative embodiment, once the peripheral electronic device is disassociated from the monitored patient, the wireless system may no longer process or store any physiological data acquired by a wireless sensor of that peripheral electronic device, until the peripheral electronic device is reregistered or verified as associated to the monitored patient.

At 214 the association confidence levels from 202 may be used in an alternative manner such that the received physiological data from each of the peripheral electronic devices is appended with the association confidence level for that peripheral electronic device at 214. As described above, the association confidence levels may be periodically re-determined at regular intervals and therefore the received physiological data may be appended with the association confidence level for that peripheral electronic device in the time interval in which the physiological data was acquired. This appended physiological data can then be stored, exemplarily at the monitored patient EMR such that the appended physiological data can be later used in patient evaluation, diagnosis or therapeutic decisions as an additional piece of information that is reflective of the quality of confidence that the physiological data was acquired by a peripheral electronic device that was actually associated with the monitored patient.

Furthermore, in some wireless systems, the clinician or technician may be provided with automated medical guidance or the patient may receive automated therapeutic interactions based upon the physiological data acquired form the monitored patient. In an embodiment, the automated actions may be desired to only be performed when there is a high level of confidence between each of the peripheral electronic devices and the monitored patient. In such embodiments, at 216 the association confidence level for each of the peripheral electronic devices are compared to a predetermined threshold. Similar to the threshold as described above with respect to 204 and 206, this threshold may exemplarily be a predetermined value based upon clinical standard for a required confidence level. In a non-limiting embodiment, the threshold at 216 may be a 95 on a normalized scale between 0-100, although this is merely exemplary of the predetermined threshold that may be used. If one or more of the confidence levels for each of the peripheral electronic devices is below the predetermined threshold, then an alarm may be initiated at 218 in order to alert the clinician or technician either that automated actions are being taken without the requisite association confidence levels or to alert the clinician or technician that some or all of the automated actions have been disabled due to insufficient confidence in the association between the peripheral electronic devices and the monitored patient. If all of the confidence levels are above the predetermined threshold, then automated actions may be taken based upon the received physiological data from the peripheral electronic devices. The automated action may exemplarily include automated medical guidance, presented to the clinician or technician at 220. Automated medical guidance may take any of a variety of forms, and specifically may include identifications of potential physiological conditions or risks identified based upon an analysis of at least in part, the acquired physiological data. In embodiments, the analysis may further extend to data stored in the patient electronic medical record, or other sources of medical data.

At 222 a further action that may be taken if the confidence levels are above the predetermined threshold at 216 may be the operation and control of an automated therapeutic interaction based upon the acquired physiological data. As described above, in some embodiments, therapeutic devices such as IV or drug pumps, ventilators, or defibrillators may be operated to automatedly take a therapeutic action based upon the acquired physiological data. As these automated therapeutic interactions may have an adverse effect on the patient health or wellbeing if an inappropriate action is taken, it may be desirable in embodiments to only provide such automated therapeutic interactions when there is a high confidence that all of the acquired physiological data analyzed to initiate the automated therapeutic interaction has been acquired by peripheral electronic devices associated with the monitored patient.

In an alternative embodiment, automated therapeutic interactions may operate on a reduced functionality depending upon the peripheral electronic device with the lowest association confidence level, and that particular level. In such an embodiment, basic adjustments or controls may be maintained at lower confidence levels, while more invasive responses may only be undertaken when there is a high confidence in all of the peripheral electronic devices. As a merely exemplary embodiment of an IV pump, under a lower confidence level, the IV pump may be operated to maintain or make minor adjustment to an IV rate, while automated adjustments between intravenously delivered substances, or the delivery of a bolus may only occur under a high confidence level with each of the peripheral electronic devices.

As referenced above, FIG. 5 depicts an exemplary embodiment of a graphical user interface 300 that may be presented on a graphical display. The GUI 300 includes a plurality of sensor indicators 302. The sensor indicators 302 may generally identify the anatomical location of the wireless sensor on the monitored patient. In an exemplary embodiment, the sensor indicators 302 may be color coded to represent an association status of the sensor based upon the confidence value, such association status may exemplarily indicate a high, medium, or low association between the wireless sensor and the monitored patient. The GUI 300 may further present the derived confidence value 304 associated with each of the wireless sensors. Thus, in embodiments such as that depicted in FIG. 5, a clinician or technician is presented with both a visual indication of a general association status as well as a more detailed confidence value indication.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A wireless patient monitoring system, comprising:
   a plurality of peripheral electronic devices each having a wireless communication system and a sensor, each of the plurality of peripheral electronic devices adapted to be secured to a monitored patient, the sensors of each of the plurality of electronic devices acquire physiological data from the monitored patient, the physiological data acquired from the monitored patient being transmitted by the wireless communication device of a respective peripheral electronic device;

a processor that registers each of the plurality of peripheral electronic devices to the monitored patient, the processor receives the physiological data from the respective peripheral electronic devices, the processor establishes an association confidence level for each peripheral electronic device based upon at least the received physiological data from each of the peripheral electronic devices, the association confidence level indicative of a likelihood that the physiological data acquired by the peripheral electronic device is from the monitored patient, the processor compares each of the association confidence levels established for each peripheral device to a predetermined threshold and if an association confidence level is below the predetermined threshold, the processor disassociates that peripheral electronic device from the monitored patient; and an indicator on each of the plurality of peripheral electronic devices, wherein the indicator produces a first indication if the association confidence level is less than the predetermined threshold and produces a second indication if the association confidence level is above the predetermined threshold.

2. The wireless patient monitoring system of claim 1, wherein the plurality of peripheral electronic devices is a first plurality of peripheral electronic devices and the monitored patient is a first monitored patient, the system further comprising:

a second plurality of peripheral electronic devices registered by the processor to a second monitored patient, wherein the processor further receives physiological data from the second plurality of peripheral electronic devices, establishes an association confidence level for each of the peripheral electronic devices of the second plurality of peripheral electronic devices, and uses the established association confidence levels to separate physiological data acquired from the first monitored patient from physiological data acquired from the second monitored patient.

3. The wireless patient monitoring system of claim 2, wherein the processor monitors system data of the plurality of peripheral electronic devices and the processor uses the system data to register the plurality of peripheral electronic devices between the first plurality of peripheral electronic devices and the second plurality of peripheral electronic devices.

4. The wireless patient monitoring system of claim 1, wherein the predetermined threshold is a second threshold and further comprising:

a first threshold defining an association confidence level greater than the second threshold;
wherein the indicator is a light emitting indicator and the on each of the plurality of peripheral electronic devices, and wherein the indicator produces the second indication if the association confidence level is below the first threshold and produces a third indication if the association confidence level is greater than the first threshold.

5. The wireless patient monitoring system of claim 1, further comprising:

a hub having a wireless communication system, the hub in wireless communication with the peripheral electronic devices and communicatively connected to the processor, the hub receives the physiological data broadcast by the respective peripheral electronic devices and provides the physiological data to the processor.

6. A wireless patient monitoring system, comprising:

a plurality of peripheral electronic devices each having a wireless communication system and a sensor, each of the plurality of peripheral electronic devices adapted to be secured to a monitored patient, the sensors of each of the plurality of electronic devices acquire physiological data from the monitored patient, the physiological data acquired from the monitored patient being transmitted by the wireless communication device of a respective peripheral electronic device;

a processor that registers each of the plurality of peripheral electronic devices to the monitored patient, the processor receives the physiological data from the respective peripheral electronic devices, the processor establishes an association confidence level for each peripheral electronic device based upon at least the received physiological data from each of the peripheral electronic devices, the association confidence level indicative of a likelihood that the physiological data acquired by the peripheral electronic device is from the monitored patient; and a plurality of indicators, each indicator of the plurality configured to communicate the association confidence level for an associated peripheral electronic device of the plurality of peripheral electronic devices, wherein an indicator of the plurality of indicators is located on each of the peripheral electronic devices and the processor is in communicative connection with the wireless communication device of each of the peripheral electronic devices, wherein the processor transmits a signal indicative of the association confidence level for a peripheral electronic device to that peripheral electronic device, and each peripheral electronic device operates the indicator of that peripheral electronic device to present the received association confidence level.

7. The wireless patient monitoring system of claim 6, wherein the plurality of peripheral electronic devices is a first plurality of peripheral electronic devices and the monitored patient is a first monitored patient, the system further comprising:

a second plurality of peripheral electronic devices registered by the processor to a second monitored patient, wherein the processor further receives physiological data from the second plurality of peripheral electronic devices, establishes an association confidence level for each of the peripheral electronic devices of the second plurality of peripheral electronic devices, and uses the established association confidence levels to separate physiological data acquired from the first monitored patient from physiological data acquired from the second monitored patient.

8. The wireless patient monitoring system of claim 7, wherein the processor monitors system data of the plurality of peripheral electronic devices and the processor uses the system data to register the plurality of peripheral electronic devices between the first plurality of peripheral electronic devices and the second plurality of peripheral electronic devices.

9. The wireless patient monitoring system of claim 6, wherein the association confidence level for each of the peripheral electronic devices of the plurality of peripheral electronic devices is further based upon system data, wherein the system data comprises at least one of a length of time since registration of the peripheral device, an RF signal strength, an elapsed time that a peripheral electronic device is detached from the monitored patient, an activity type, a number of communication errors, a battery state, a location of the peripheral electronic device, an elapsed time the peripheral electronic device is secured to a patient, a movement of the peripheral electronic device.

10. The wireless patient monitoring system of claim 9, wherein the physiological data received from at least one of the peripheral devices comprises at least one of: electrocardiogram, electromyogram, electroencephalogram, temperature, respiration, blood oxygenation (SpO2), blood pressure, movement, heart rate, and pulse rate.

11. A method of workflow management in a wireless patient monitoring system, the method comprising:
providing a plurality of peripheral electronic devices, each comprising a communication system and a sensor configured to acquire physiological data from a patient;
registering, at a processor, each of the plurality of peripheral electronic devices to a monitored patient;
receiving physiological data acquired by each of the peripheral electronic devices at the processor;
applying at least one association criteria to the physiological data to derive physiological association criteria values;
collecting system data from each of the peripheral electronic devices of the plurality of peripheral electronic devices;
applying a plurality of association criteria to the collected system data to produce system association criteria values;
determining an association confidence level for each of the peripheral electronic devices based at least in part upon the physiological association criteria values and the system association criteria values.

12. The method of claim 11, further comprising:
providing therapy to the patient with a therapeutic device controlled by the processor based at least in part upon the received physiological data.

13. The method of claim 11, further comprising:
appending the association confidence levels established for each peripheral electronic device to the received physiological data acquired by that peripheral electronic device; and
storing the association confidence level with the received physiological data.

14. The method of claim 11, further comprising:
operating a graphical display communicatively connected to the processor to present the association confidence level for each of the peripheral electronic devices.

15. A method of workflow management in a wireless patient monitoring system, the method comprising:
providing a plurality of peripheral electronic devices, each comprising a communication system and a sensor configured to acquire physiological data from a patient;
registering, at a processor, each of the plurality of peripheral electronic devices to a monitored patient;
receiving physiological data acquired by each of the peripheral electronic devices at the processor;
applying at least one association criteria to the physiological data to derive association criteria values;
determining an association confidence level for each of the peripheral electronic devices based at least in part upon the association criteria values; and
operating an indicator on each of the peripheral electronic devices to present the association confidence level for that peripheral electronic device.

16. A method of workflow management in a wireless patient monitoring system, the method comprising:
providing a plurality of peripheral electronic devices, each comprising a communication system and a sensor configured to acquire physiological data from a patient;
registering, at a processor, each of the plurality of peripheral electronic devices to a monitored patient;
broadcasting the acquired physiological data from the communication systems of each of the peripheral electronic devices;
receiving the broadcast acquired physiological data at a wireless communication system in communication with the communication systems of each of the peripheral electronic devices;
receiving physiological data acquired by each of the peripheral electronic devices at the processor from the wireless communication system;
applying at least one association criteria to the physiological data to derive association criteria values;
determining an association confidence level for each of the peripheral electronic devices based at least in part upon the association criteria values;
transmitting a signal indicative of the association confidence level for a peripheral electronic device of the plurality of peripheral electronic devices;
receiving the signal at the peripheral electronic device; and
operating an indicator of the peripheral electronic device to present the association confidence level at the peripheral electronic device.

17. A method of workflow management in a wireless patient monitoring system, the method comprising:
providing a plurality of peripheral electronic devices secured to one of a first patient and a second patient, each peripheral electronic device comprising a communication system and a sensor configured to acquire physiological data from the first patient or the second patient;
registering, at a processor, each of the plurality of peripheral electronic devices to a monitored patient;
receiving at the processor physiological data from the first patient and the second patient acquired the peripheral electronic devices;
applying at least one association criteria to the physiological data to derive association criteria values wherein the at least one association criteria compares the physiological data received from each of the peripheral electronic devices to associate each of the peripheral electronic devices to the first patient or the second patient; and
determining an association confidence level for each of the peripheral electronic devices based at least in part upon the association criteria values and the peripheral electronic devices associated to the same patient of the first patient and the second patient.

18. The method of claim 17, further comprising:
providing therapy to the patient with a therapeutic device controlled by the processor based at least in part upon the received physiological data.

19. The method of claim 17, further comprising:
appending the association confidence levels established for each peripheral electronic device to the received physiological data acquired by that peripheral electronic device; and
storing the association confidence level with the received physiological data.

20. The method of claim 17, further comprising:
operating a graphical display communicatively connected to the processor to present the association confidence level for each of the peripheral electronic devices.

* * * * *